US00PP14766P3

(12) United States Plant Patent
van Os

(10) Patent No.: US PP14,766 P3
(45) Date of Patent: May 4, 2004

(54) ROSA PLANT NAMED 'SELIRON'

(50) Latin Name: *Rosa L.*
Varietal Denomination: Seliron

(75) Inventor: Diana Petronella Maria van Os, Bleiswijk (NL)

(73) Assignee: Terra Nigra Holding B.V., De Kwakel (NL)

( * ) Notice: Subject to any disclaimer, the term of this patent is extended or adjusted under 35 U.S.C. 154(b) by 11 days.

(21) Appl. No.: 10/307,572

(22) Filed: Dec. 2, 2002

(65) Prior Publication Data

US 2003/0135902 P1 Jul. 17, 2003

(51) Int. Cl.[7] ..... A01H 5/00

(52) U.S. Cl. ..... Plt./140

(58) Field of Search ..... Plt./140

*Primary Examiner*—Anne Marie Grunberg

*Assistant Examiner*—Susan B. McCormick

(57) ABSTRACT

A new rose of the Hybrid Tea class, characterized by its continuous good production of dark red flowers having a very good presentation in bud as well as open flower, borne singly on upright long stems on a bush of medium height, and healthy foliage.

1 Drawing Sheet

BACKGROUND OF THE INVENTION

The present invention relates to a new and distinct variety of rose plant of the Hybrid Tea class, which was originated by me by crossing the unnamed seedling SR89.013 (not patented) (seed parent) with 'Black Magic' (not patented) (pollen parent). The female parent (pink, hybrid T, very productive) has passed its good characteristicof growth, but differs clearly from the present invention by color and flower shape. The male parent is a darker red then 'Seliron' with glossy foliage. This crossing was carried out in a greenhouse in De Kwakel.

The primary objective of this breeding was to obtain a new Hybrid-T type rose with a good presentation and budshape in different colors. Among the novel characteristics possessed by the new variety which distinguish it from its parents and all other varieties of which I am aware are:

1) A very large flower and flowerbud.

2) The warm red color of the flower.

3) Rapid growth of the plant.

4) Long flower stems.

5) Suitability for growing in many different areas.

Asexual reproduction of the new rose variety by cutting and grafting using 'Natal Briar' (not patented) as rootstock, as performed in a greenhouse in De Kwakel, The Netherlands, shows that the aforementioned characteristics and distinctions come true to form and are established and transmitted through succeeding propagations.

BRIEF DESCRIPTION OF THE DRAWING

The new variety of rose plant is illustrated by the accompanying photographic illustration, which shows typical specimens of the flowers of the new variety in different stages of development and as depicted in color as nearly true as is reasonably possible to attain in illustrations of this type.

BOTANICAL DESCRIPTION OF THE PLANT

Botanical: *Rosa L.* cv. 'Seliron'.

The following is a detailed description of this new variety, with color terminology in accordance with The Royal Horticultural Society Colour Chart (R.H.S.C.C.). The terminology used in the color description herein refers to plate numbers in the aforementioned color chart e.g "55C" is plate "55C" of The Royal Horticultural Society Colour Chart.

Observations are made from specimens grown in a greenhouse in De Kwakel, The Netherlands, on a one year old plant. The color values were determined at 9:00 am on Nov. 26, 2002 under artificial light at De Kwakel. The following traits have been repeatedly observed and are determined to be basic characteristics of 'Seliron', which in combination distinguish this Rosa as a new and distinct cultivar.

INFLORESCENCE

Blooming habit of 'Seliron': Almost continuous.
Time of beginning of flowering: Very early.
A. Bud:

*Size.*—Large. Diameter 3.0–3.5 cm. Length 5.0–5.3 cm.

*Form.*—Ovoid.

*Color.*—When the sepals first divide, the color of the outside is red, RHS 53A.

*Sepals.*—Shape: 30 to 32 mm. Hooded over. Stand up when open. Color: inside: light green, RHS 144B. Outside: green, RHS 144A. Hairs on inner surface: many. On outer surface: few.

*Phyllaries.*—Number: medium (2–3). Shape: elliptic, 10×2 mm. Color: light brown, RHS 42B.

*Calyx.*—Color: green, RHS 144A. Shape: funnelshaped. Size: medium: diameter: average 10 mm. Aspect: smooth. Odor when rubbed: present.

*Rate of opening.*—Normal.

*Peduncle.*—Length: medium to long (9 to 11 cm). Aspect: smooth. Strength: medium. Color: green, RHS 144A.

*Openings.*—Opens up normally, almost completely; is not affected by adverse weather.

B. Bloom:

*Size.*—Large. When fully expanded about 9–10 cm in diameter with a depth of about 4.5–5.0 cm.

*Borne.*—Single.

*Stems.*—Length: 90–110 cm. Strength: medium.

*Form* (*when first open*).—Starshaped. Permanence: good.

*Petalage.*—Number of petals: average 30–35.

*Color.*—Center of flower: red, RHS 46A. Outer petals: red, RHS 46A. Base of petals: red, RHS 46B. Spot at the base: present, light yellow RHS 4D. Inside of petals: red, RHS 46A. Reverse of petals: red, RHS 45B. General tonality: red, RHS 46A.

*Discoloration.*—General tonality not changing when aging.

C. Petals:

*Texture.*—Leathery; is not affected by wet or hot weather.

*Appearance.*—Inside: satiny. Outside: satiny.

*Form.*—Broad ovate. Reflexing of margin: medium. Undulation of margin: medium.

*Arrangement.*—Regular.

*Petaloids in center.*—Number: 3. Size: large. Color: base red, RHS 46A. Middle and marginal zone red, RHS 46A.

*Persistence.*—Drops off cleanly.

*Fragrance.*—Weak herbal like scent.

*Lasting quality.*—On the plant: 12–16 days. As cut-flower: 10–12 days.

REPRODUCTIVE ORGANS

A. Stamens:

*Arrangement.*—Regular, below stigma.

*Number.*—Average close to 100.

*Length.*—8–9 mm.

*Anthers.*—Size: medium (2–3 mm). Color: yellow-orange, RHS 23B.

*Filaments.*—Length: medium (7–8 mm). Color: base of anthers: light yellow, RHS 4C. Lower filament: light yellow RHS 4C.

*Pollen.*—Color: yellow, RHS 2B.

B. Pistils:

*Styles.*—Number: average close to 60. Length: 9–10 mm. Color: lower part (50%) cream white RHS 4D, upper part red/pink RHS 51A.

*Stigmas.*—Color: yellow, RHS 11B.

*Fruit.*—Fertility: normal. Shape: ovoid. Color at maturity: orange RHS 25A.

PLANT

A. Form: Bed rose.

B. Growth: Upright.

C. Height: Medium to high (110–130 cm).

D. Width: Medium (30–35 cm).

D. Foliage: 12 to 15 compound leaves on bloom stem.

*Size.*—Medium.

*Quantity.*—Average.

*Color.*—New foliage: upper side: red brown, RHS 200B. Under side: brownish, RHS 177A. Old foliage: upper side: dark green, RHS 147A. Under side: green, RHS 148B.

*Texture.*—Upper side: leathery. Under side: dull.

*Terminal leaflet.*—Shape: elliptic, base obtuse. Size: medium. Length: 78–82 mm. Diameter: 50–52 mm. Length petiole: 19–21 mm.

*Ribs and veins.*—Lighter green, RHS 145A.

*Rachis.*—Upper side: green, RHS 147A. Lower side: green, RHS144A.

*Margin type.*—Medium serrate, 4 points/cm, 1–2 mm peak.

*Stipules.*—Length: average 16–18 mm, auricle to 6 mm. Texture: smooth. Color: brown, RHS 177A.

E. Resistance to diseases: Normal resistance to common diseases, resistant to powdery mildew.

F. Drought tolerance: No specific tolerance against drought.

G. Heat tolerance: Yes, more than average.

H. Wood:

*New wood.*—Color: red brown, RHS 178A. Bark: smooth.

*Old wood.*—Color: dark green, RHS 146A. Bark: smooth.

I. Thorns:

*Quantity.*—Medium to many. On main stalks from base: many. On laterals from stalk: medium.

*Form.*—Deep concave.

*Length.*—Large (10 mm–12 mm).

*Hooked.*—Downward.

*Color* (*when young*).—Red brown, RHS 181A.

*Position.*—Irregular.

J. Prickles:

*Quantity.*—Medium to many. On peduncle: lower half medium to many. On rachis: few.

K. Short needles:

*Quantity.*—Absent or very few.

I claim:

1. A new and distinct cultivar of Rosa plant named 'Seliron' of the Hybrid Tea class, substantially as herein shown and described, characterized by its continuous good production of warm red flowers having a very good presentation in bud as well as open flower, borne singly on upright long stems on a bush of medium height, and healthy foliage, showing rapid growth of the plant and is particularly suitable to grow in many different areas.

* * * * *

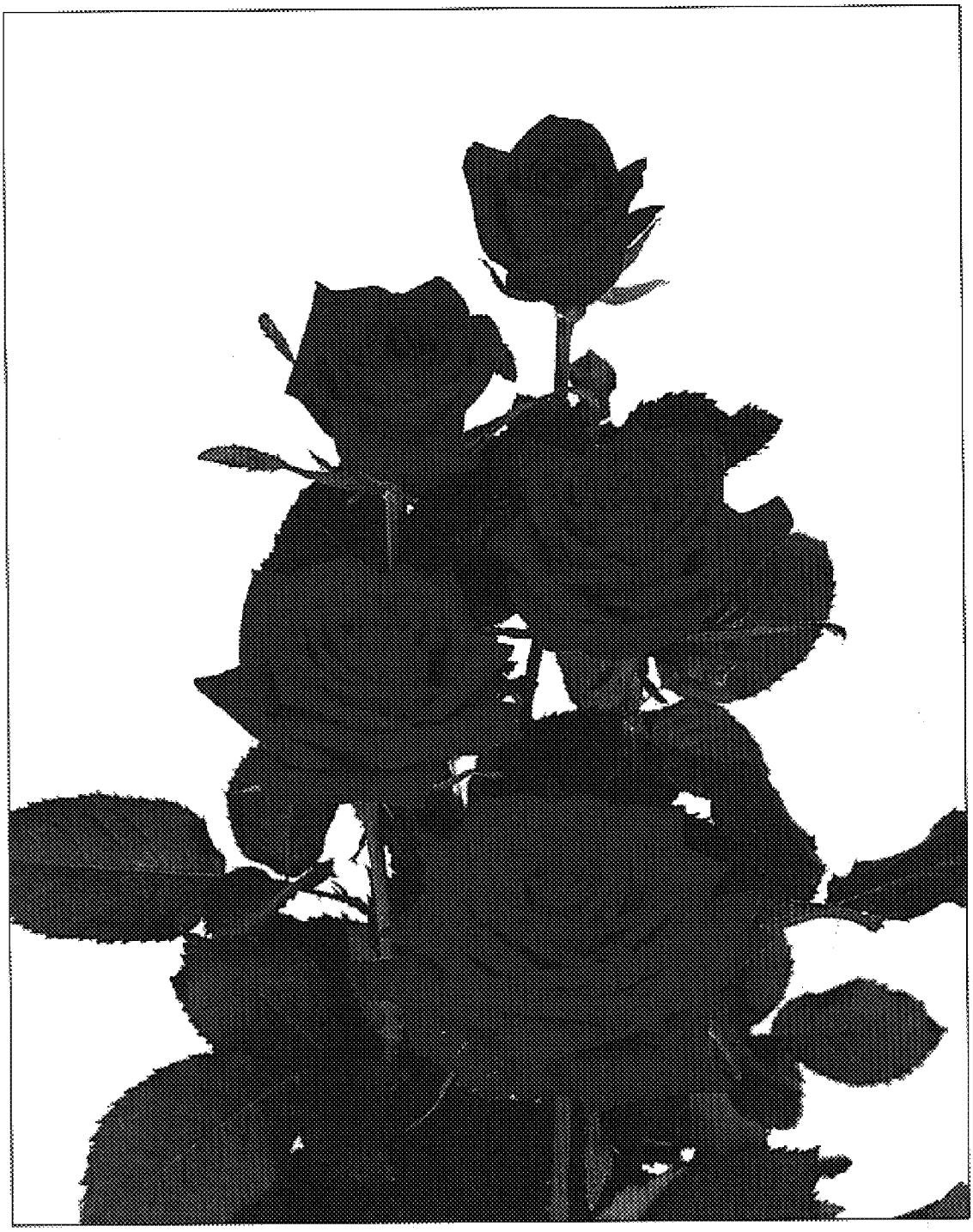

Title of invention: Rosa plant named 'Seliron'